United States Patent
Alexander-Friedrich

(10) Patent No.: US 10,400,217 B2
(45) Date of Patent: Sep. 3, 2019

(54) IMMORTALIZED CELL

(71) Applicant: Eberhard Karls Universitaet Tuebingen Medizinische Fakultaet, Tuebingen (DE)

(72) Inventor: Dorothea Alexander-Friedrich, Stuttgart (DE)

(73) Assignee: EBERHARD KARLS UNIVERSITAET TUEBINGEN MEDIZINISCHE FAKULTAET, Tuebingen (DE)

( * ) Notice: Subject to any disclaimer, the term of this patent is extended or adjusted under 35 U.S.C. 154(b) by 0 days.

(21) Appl. No.: 15/236,266

(22) Filed: Aug. 12, 2016

(65) Prior Publication Data

US 2016/0348075 A1   Dec. 1, 2016

Related U.S. Application Data

(63) Continuation of application No. PCT/EP2015/053213, filed on Feb. 16, 2015.

(30) Foreign Application Priority Data

Feb. 14, 2014   (DE) ........................ 10 2014 101 862

(51) Int. Cl.
   *C12N 5/10*   (2006.01)
   *C12N 5/077*   (2010.01)
   *C12N 7/00*   (2006.01)

(52) U.S. Cl.
   CPC ......... *C12N 5/0654* (2013.01); *C12N 5/0656* (2013.01); *C12N 7/00* (2013.01); *A61L 2430/02* (2013.01); *C12N 2501/998* (2013.01); *C12N 2510/04* (2013.01); *C12N 2710/22022* (2013.01); *C12N 2740/15043* (2013.01)

(58) Field of Classification Search
   None
   See application file for complete search history.

(56) References Cited

U.S. PATENT DOCUMENTS

2008/0288085 A1* 11/2008 Mao .................... A61L 27/3804
                                                           623/23.72

FOREIGN PATENT DOCUMENTS

| EP | 1207196 | 5/2002 |
|----|---------|--------|
| WO | WO-99/39724 | 8/1999 |
| WO | WO-00/21523 | 4/2000 |
| WO | WO-02/34891 | 5/2002 |

OTHER PUBLICATIONS

Chano et al., Periosteal osteosarcoma and parosteal chondrosarcoma evaluated by double immunohistochemical staining. Acta Orthop Scand 1994; 65 (3): 355-358 (Year: 1994).*
Hanahan et al., The Hallmarks of Cancer. Cell, vol. 100, 57-70, Jan. 7, 2000 (Year: 2000).*
Robertson et al., Periosteal Osteosarcoma of the Cranium. Annals of Diagnostic Pathology, vol. 4, No. 5 Oct. 2000: pp. 300-302 (Year: 2000).*
Li et al., Experimental study on rabbit periosteal osteoblasts and renal vascular endothelial cells indirect co-culture in vitro. Chinese Journal of Reparative and Reconstructive Surgery. Sep. 2002;16(5):307-10. (Year: 2002).*
Cao et al., "Characterization of immortalized mesenchymal stem cells derived from foetal porcine pancreas," Cell Prolif (2011) 44(1):19-32.
Darimont et al., "SV40 T antigen and telomerase are required to obtain immortalized human adult bone cells without loss of the differentiated phenotype," Cell Growth Differ (2002) 12(2):59-67.
Gong et al., "Immortalized mesenchymal stem cells: an alternative to primary mesenchymal stem cells in neuronal differentiation and neuroregeneration associated studies," Journal of Biomedical Science (2011) 18:87.
Huang et al., "Conditionally immortalized mouse embryonic fibroblasts retain proliferative activity without compromising multipotent differentiation potential," PLoS One (2012) 7(2):e32428.
Komine et al., "Establishment of adipose-derived mesenchymal stem cell lines from a p53-knockout mouse," Biochemical and Biophysical Research Communications 426(4):468-474.
Moscoso et al., "Immortalization of bone marrow-derived porcine mesenchymal stem cells and their differentiation into cells expressing cardiac phenotypic markers," J Tissue Eng Regen Med (2012) 6(8):655-665.
Ramakrishnan et al., "Primary marrow-derived stromal cells: isolation and manipulation," Methods Mol Biol 2013 1035:75-101.
Sreejit et al., "Generation of mesenchymal stem cell lines from murine bone marrow," Cell Tissue Res (2012) 350(1):55-68.
Xiaoxue et al., "Immortalization of human osteoblasts by transferring human telomerase reverse transcriptase gene," Biochem Biophys Res Commun (2004) 315(3):643-651.
Yalvac et al., "Differentiation and Neuro-Protective Properties of Immortalized Human Tooth Germ Stem Cells," Neurochem Res 36(12):2227-2235.
Zamperone et al., "Isolation and characterization of a spontaneously immortalized multipotent mesenchymal cell line derived from mouse subcutaneous adipose tissue," Stem Cells Dev (2013) 22(21):2873-2884.

* cited by examiner

*Primary Examiner* — Kevin K Hill
*Assistant Examiner* — Arthur S Leonard
(74) *Attorney, Agent, or Firm* — Rimon, P.C.

(57) ABSTRACT

The present invention relates to an immortalized cell, an immortalized cell line comprising said immortalized cell, a cell culture comprising the immortalized cell or cell line, and a method for the production of an immortalized cell.

3 Claims, 9 Drawing Sheets

A

Alkaline Phosphatase Gene Expression

B

Osterix Gene Expression

IMMORTALIZED CELL

CROSS-REFERENCE TO RELATED APPLICATIONS

This application is a continuation of copending international patent application PCT/EP2015/053213 filed on 16 Feb. 2015 and designating the U.S., which has been published in German, and claims priority from German patent application DE 10 2014 101 862.1 filed on 14 Feb. 2014. The entire contents of these prior applications are incorporated herein by reference.

FIELD OF THE INVENTION

The present invention relates to an immortalized cell, an immortalized cell line comprising said immortalized cell, a cell culture comprising the immortalized cell or cell line, and a method for the production of an immortalized cell.

BACKGROUND OF THE INVENTION

In the fundamental research larger amounts of cell material for in vitro experiments are needed, for example to execute functional assays or to analyze the adhesion and proliferation behavior, the gene and protein expression. Also in application-oriented disciplines of life sciences there is a need of cell material, for example for the so-called tissue engineering or the cell therapy.

Since cell donors cannot be strained permanently with tissue removal, the current availability of cell material, particularly of human origin, is unsatisfactory.

Primary cells, i.e. those cells that were isolated from an immediately previously still intact organ or tissue, have the disadvantage that their ability to divide is limited. In higher passages often the so-called cell senescence occurs. This applies especially to human primary cells. In this context it is spoken of the so-called Hayflick limit which refers to the limited number of cell divisions in eukaryotes, which a cell may undergo. Upon reaching this limit the programmed cell death is initiated because the telomeres reach a critically reduced length.

A certain advantage have stem cells which initially comprise strong proliferation ability, however, their availability is also limited by the occurrence of cell senescence in higher passages. In addition, stem cells, especially those of mesenchymal character, increasingly lose their differentiation ability in higher passages and are therefore only suitable to a limited extent for the purpose mentioned at the outset and especially for the examination of the differentiation processes.

In order to overcome these limits, immortalized cell lines from different tissue types were generated, "Immortalization" shall be understood as the immortal-making of cells. The limitation of the number of cell divisions by the Hayflick limit is abrogated thereby. Immortalized cells, or cell lines, respectively, may divide any number of times in contrast to normal cells and can proliferate in cell culture in an unlimited manner. An immortalization may be reached, for example, by an infection of the cells with particular viruses, i.e. by viral transduction or by fusion with tumor cells. Immortalized cells often retain the self-function of primary cells from which they were generated.

RELATED PRIOR ART

Currently only relatively few immortalized cells are available, mostly murine, porcine, and human mesenchymal stem cells which were withdrawn from the bone marrow (BMMSCs) and then immortalized. Furthermore, stem cells from fetal porcine pancreas, murine embryonic fibroblasts and from murine adipose tissues were isolated and subsequently immortalized; see Cao et al. (2011), "Characterization of immortalized mesenchymal stem cells derived from foetal procine pancreas" Cell Prolif 44(1): 19-32; Gong et al. (2011), "Immortalized mesenchymal stem cells: an alternative to primary mesenchymal stem cells in neuronal differentiation and neuroregeneration associated studies" Journal of Biomedical Science 18; Yalvac et al. (2011), "Differentiation and neuro-protective properties of immortalized human tooth germ stem cells" Neurochem Res 36(12):2227-2235; Huang et al. (2012), "Conditionally Immortalized Mouse Embryonic Fibroblasts Retain Proliferative Activity without Comprising Multipotent Differentiation Potential" Plos One 7(2); Komine et al. (2012), "Establishment of adipose-derived mesenchymal stem cell lines from a p53-knockout mouse" Biochem Biophys Res Commun 426(4): 468-474; Moscoso et al. (2012), "Immortalization of bone marrow-derived porcine mesenchymal stem cells and their differentiation into cells expressing cardiac phenotypic markers" Journal of Tissue Engineering and Regenerative Medicine 6(8):655-665; Sreejit et al. (2012), "Generation of mesenchymal stem cell lines from murine bone marrow" Cell Tissue Res 350(1):55-68; Ramakrishnan et al. (2013), "Primary marrow-derived stromal cells: isolation and manipulation" Methods Mol Biol 1035: 75-101; Zamperone et al, (2013), "Isolation and Characterization of a Spontaneously Immortalized Multipotent Mesenchymal Cell Line Derived from Mouse Subcutaneous Adipose Tissue" Stem Cells Dev.

In the WO 02/34891 a human immortalized cell line referred to as hPOBtert is disclosed, which is osteogenically differentiated according to the information of the authors. It is derived from the periosteum of a 13-years-old patient.

Thus, a strong need for immortalized cells further exists.

SUMMARY OF THE INVENTION

Against this background, it is an object of the present invention to provide a further immortalized cell or an immortalized cell line and cell culture comprising such a cell, in order to satisfy the need in the state of the art.

This object is achieved by the provision of an immortalized periosteum cell, an immortalized periosteum cell line and a cell culture which comprises immortalized periosteum cells.

"Periosteum" or also "bone skin" refer to the bone covering connective tissue-like integument. The periosteum serves to the protection of the bone, in addition it is the attachment side for ligaments and tendons. The periosteum consists of an outer collagen layer with elastic fibers and an inner layer which contains nerves and blood vessels and mesenchymal precursor cells. The precursor cells may differentiate into different directions after an appropriate stimulation. The periosteum has a special importance in the natural bone healing.

The objects underlying the invention are herewith completely achieved.

The inventor provides for the first time an immortalized periosteum cell or an immortalized periosteum cell line or cell culture composed of immortalized periosteum cells. The cells according to the invention allow the execution of experiments and application-related operations without the occurrence of patient-related fluctuations which are known from the use of primary cells. Thereby, the reproducibility of the results is increased. The cells according to the invention are easier in handling than primary cells. Furthermore, the problem of cell senescence does not occur. The cells according to the invention proliferate in an unlimited manner.

The immortalized periosteum cell according to the invention is especially suitable for the examination of the osteogenesis and mineralization, but also for research of processes of cell adhesion, proliferation and apoptosis and the healing of wounds.

According to the invention, "immortalized periosteum cell" shall be understood as such a cell which was obtained by the immortalization of periosteum cells or derived from the periosteum. "Immortalization" refers to the immortal-making of cells, for example by viral infection, transduction with oncogene products such as the large T-antigen of SV40, or by fusion with tumor cells, as described above.

In an embodiment of the invention, the immortalized periosteum cell is a human immortalized periosteum cell.

This measure has the advantage that the cell according to the invention is particularly well suited for examinations, which should allow the drawing of conclusions on processes in the human organism. Here, in this context "human" means that the primary periosteum cells which were immortalized are of human origin.

In another embodiment of the invention, the immortalized periosteum cell is an immortalized cranium periosteum cell.

According to this embodiment the primary cells from the periosteum of the cranium bone, were immortalized. This measure has the advantage that, according to the knowledge of the inventor, a particularly suitable immortalized periosteum cell is provided.

Further, according to another embodiment of the invention, the immortalized periosteum cell is osteogenically differentiable.

According to the invention, "osteogenically differentiable" means that the cell comprises the potential to develop into a bone tissue forming cell. Osteogenically differentiated cells are, inter alia, characterized by the gene expression of osteogenesis markers, such as the transcription factors osterix and runx-2 or the peptide hormone osteocalcin. The osteogenic differentiation may for example be induced by the incubation of the cell according to the invention with bone-specific growth factors and cytokines. This measure has the advantage that the cell or cell culture according to the invention is particularly suitable in the fundamental research to analyze and decode processes of osteogenesis, mineralization and bone healing.

A further subject-matter of the present invention is an immortalized periosteum cell or immortalized periosteum cell line or cell culture which was deposited on 29 Nov. 2013 under the designation "Tag58" at the Deutsche Sammlung von Mikroorganismen and Zellkulturen GmbH, Inhoffenstraße 7B, 3124 Braunschweig, Germany (DSMZ) under the accession number DSM ACC3218. Further, the deposit was made under the provisions of the Budapest Treaty.

This measure has the advantage that such a periosteum cell or periosteum cell line according to the invention is provided, which comprises special and surprising properties. The deposited cell line according to the invention was generated from human primary cranium periosteum cells. These were transduced lentivirally with the large T-antigen of the SV40 virus. According to the used transduction protocol a conditioned immortalization of cells was expected. Thus, the immortalized jaw periosteum cells should remain at 33° C. in immortalized state, while at higher temperatures of for example 37° C. to 39° C. an inactivation of the large T-antigen was expected and the cells should reach their "basic state" again. Surprisingly, however, it turned out that the deposited cells are permanently immortalized and independent of the cultivation temperature. Further, it was surprisingly demonstrated, that the deposited cells are even more osteogenically differentiated than the primary cranium periosteum cells from which they were obtained. Therefore, the deposited cells according to the invention are particularly suitable for the intended purpose.

Against this background, the invention also relates to the use of an immortalized periosteum cell for the examination of the osteogenesis, mineralization and bone healing, wherein the use of the immortalized periosteum cell according to the invention is preferred.

The features, characteristics and advantages of the immortalized periosteum cell according to the invention apply likewise to the immortalized periosteum cell line according to the invention and the cell culture according to the invention and the use according to the invention.

A further subject-matter of the present invention relates to a method for the production of an immortalized periosteum cell, comprising the following steps:
  1. providing an isolated periosteum cell, and
  2. immortalizing the periosteum cell.

With the method according to the invention an immortalized periosteum cell or cell line according to the invention can be produced reproducibly. Thereby, the immortalization may occur by methods known by a person skilled in the art, for example by the introduction of oncogenes or the turning off of tumor suppressor genes. Further, the immortalization may occur by infection of the periosteum primary cell with certain viruses, such as for example the SV40 virus.

In an embodiment of the invention the immortalization occurs by transduction of the large T-antigen of SV40 virus into the periosteum primary cell.

This measure has the advantage that an established method for generating an immortalized cell or cell line is used, which is particularly suitable according to the knowledge of the inventor.

A further subject-matter of the present invention relates to an immortalized periosteum cell which is obtainable by the method for the production of an immortalized periosteum cell according to this invention.

The features, characteristics and advantages of the above-mentioned immortalized periosteum cell apply likewise to the thus obtained immortalized periosteum cell.

It goes without saying that the features mentioned before and those to be mentioned in the following cannot only be used in the respectively indicated combination but also in other combinations or in isolated position without departing from the scope of the present invention.

The present invention is now explained in more detail by means of embodiments which result in further features, characteristics and advantages. The embodiments are purely illustrative and do not restrict the scope of the invention. Reference is made to the enclosed figures:

DESCRIPTION OF PREFERRED EMBODIMENTS

1. Material and Methods

Figure 1:
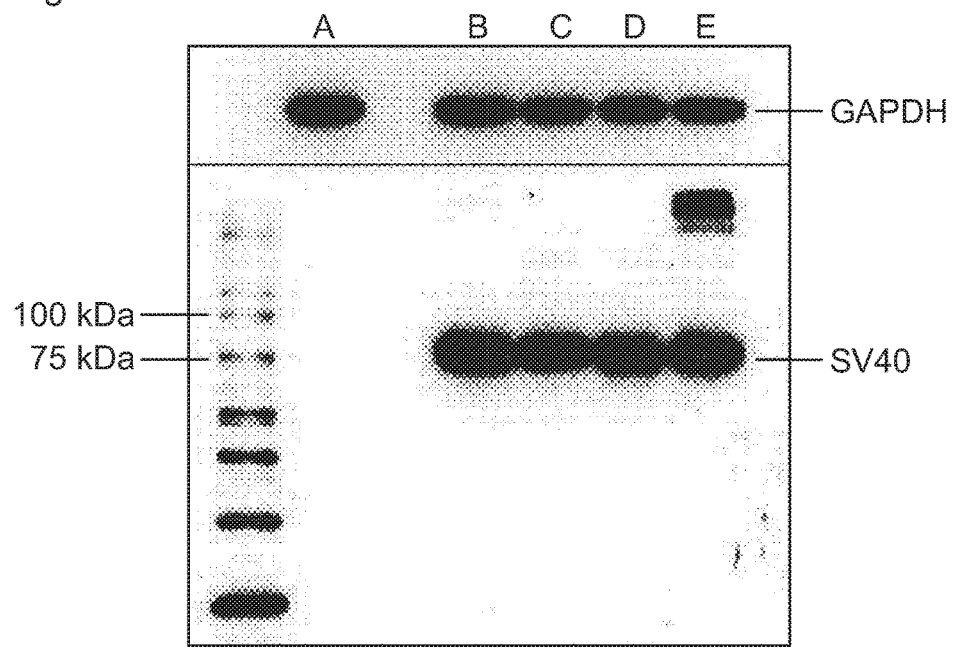
FIG. 1 shows a Western blot for detection of the permanent immortalization state of the periosteum cell according to the invention ("Tag58") via the detection of the large T-antigen of SV40. A: Primary cranium periosteum cells ("M58") at 37° C.; B: TAg58 at 33° C.; C: TAg58 at 37° C.; D: TAg58 at 38° C.; E: TAg58 at 39° C.

Lentiviral Transduction of Primary Cranium Periosteum Cells

Primary cranium bone skin cells or cranium periosteum cells (8 aliquots of $5.0 \times 10^8$ cells) were sent on dry ice to the company Sirion Biotech, Martinsried, Germany, which lentivirally transduced them. This occured by using the vector Lenti_pCDH-CMV-LTtsA58-EF1-Neo replic.-defic., self-inactivating 3rd generation lentiviral vector.

72 hours after the transduction the selection of the transduced cells with 0.50 mg/ml G418 was started. Under this selection pressure the cells were cultivated for 10 days and then cryopreserved (in Cryo-SFM medium of Promocell, C-29912). Non-transduced cells died after 5 days of cultivation in the geneticin-(G418)-containing medium. After thawing the cells maintain the immortalization state at 37° C.

The induction of the osteogenic differentiation was carried out by the addition of 4 µM dexamethasone, 10 mM β-glycerophosphate disodium salt hydrate and 100 µM ascorbic acid (L-ascorbic acid 2-phosphate). The formation of calcium phosphate precipitates by the cell monolayer is already visible after 15 days.

As already described above, the primary cells were isolated from the cranium bone skin. First, the tissue was mechanically comminuted, then the enzymatic digestion of the tissue occurred with type XI collagen for 90 min. The individual cells were cultured in 75 cm² tissue culture bottles in DMEM:Ham's F12 (1:1 mixture)+10% FCS+1% Pen-Strep+fungicides.

The expressed transgene is the cDNA of the large T-antigen (LTtsA58) of polyomavirus SV40. 72 hours after the transduction of the primary cranium periosteum cells the latter were selected for 10 days in the presence of the antibacterially active substance geneticin ((3-418; 0.5 mg/ml) and then cryopreserved.

The cells were subjected to an immortalization protocol which should lead to a conditioned immortalization. Accordingly, it was expected that a cell cultivation at 33° C. is necessary for maintaining the immortalization state. At higher temperatures of about 37° C. to 39° C. the transgene should be deactivated and the cells should acquire their "basic state" again. However, surprisingly this could not be verified in the experiments of the inventor. The cells showed an immortalization state regardless of the cultivation temperature.

In order to improve comparability of the results, both immortalized and primary cells were cultured and examined at 37° C.

So generated immortalized cranium periosteum cells were frozen and sent to the Leibnitz-Institut Deutsche Sammlung von Mikroorganismen und Zellkulturen GmbH (DSMZ), Inhoffenstraße 7B, 38124 Braunschweig, Germany. There, the viability and purity of the material was confirmed. The cell culture with the designation "Tag58" was officially deposited at the DSMZ on 29 Nov. 2013 under the accession number DSM ACC3218.

2. Results

Detection of the Immortalization State by Means of Western Blotting

In order to prove that the generated Tag58 cells are actually immortalized, the large T-antigen of SV40 was detected at the protein level in the lysates of the cells by Western blotting.

Due to the aim for conditioned immortalization it was assumed that the large T-antigen of SV40 can be detected only in cultured cells at 33° C. and not at other incubation temperatures, such as 37° C., 38° C. or 39° C. However, this could not be verified (see FIG. 1). The SV40 T-antigen was detectable independent of the incubation temperature in all samples of the immortalized cell line (lanes B to E). In the cell lysate of the parental primary cells no specific SV40 T-antigen signal was detectable (lane A).

The expected size of the specific SV40 T-antigen band of about 80 kDa was verified. As an internal control the housekeeping protein GAPDH was used.

Figure 2:
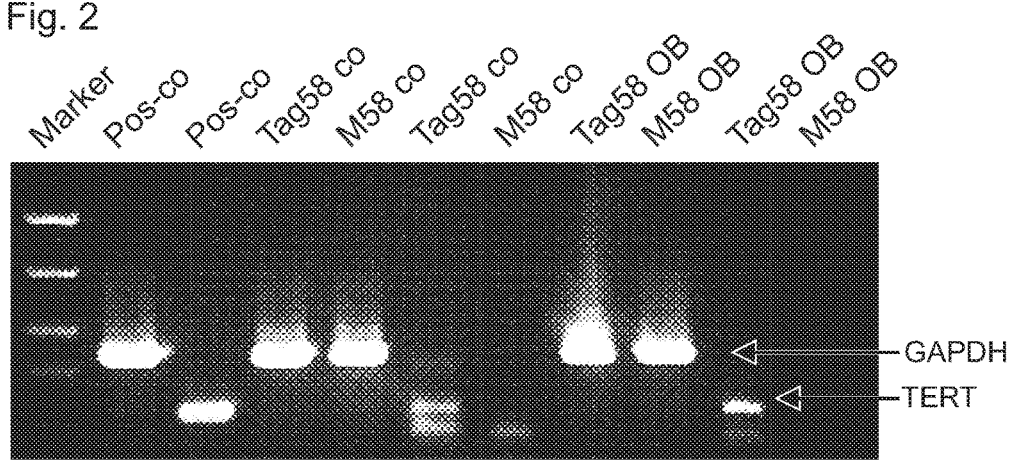
FIG. 2 shows the result of a quantitative PCR for the detection of the gene expression of the human telomerase reverse transcriptase (hTERT). Posco: positive control; Tag58 co: Tag58 undifferentiated; M58 co: M58 undifferentiated; TAg58 OB: Tag58 osteogenically stimulated (day 10); M58 OB: M58 osteogenic stimulated (day 10)

Detection of the Gene Expression of Human Telomerase Reverse Transcriptase (hTERT) by Means of Quantitative PCR In order to test whether the SV40 large T-antigen integrated into the genome is actually functionally active, the gene expression of p53 and hTERT was examined by quantitative PCR, For this purpose the Tag58 cells according to the invention were osteogenically stimulated. The induction of osteogenic differentiation occured by the addition of 4 µM dexamethason, 10 mM β-glycerophosphate disodium salt hydrate and 100 µM ascorbic acid pascorbic acid 2-phosphate). For the mRNA levels of p53 no significant differences were detected in the Tag58 cells in comparison to the parental M58 primary cells. In contrast to this, however, the hTERT gene expression could be detected only in the Tag58 cells (see FIG. 2). The specific hTERT band showed at day 10 an even stronger signal in the osteogenically stimulated Tag58 cells (Tag58 OB).

Both in the undifferentiated (M58 Co) and the osteogenically stimulated parental M58 cells (M58 OB) no specific signal for hTERT was detected.

Detection of the Gene Expression of Osteogenic Relevant Markers by Means of Quantitative PCR The gene expression of the early osteogenesis marker alkaline phosphatase and the transcription factors osterix and runx-2 and the late osteogenesis marker osteocalcin was quantitated by means of PCR. The expression of the osteogenic differentiation was examined at the beginning (day 3; T3) in the middle (day 10; T10) and at the end (day 20; T20).

Figure 3:
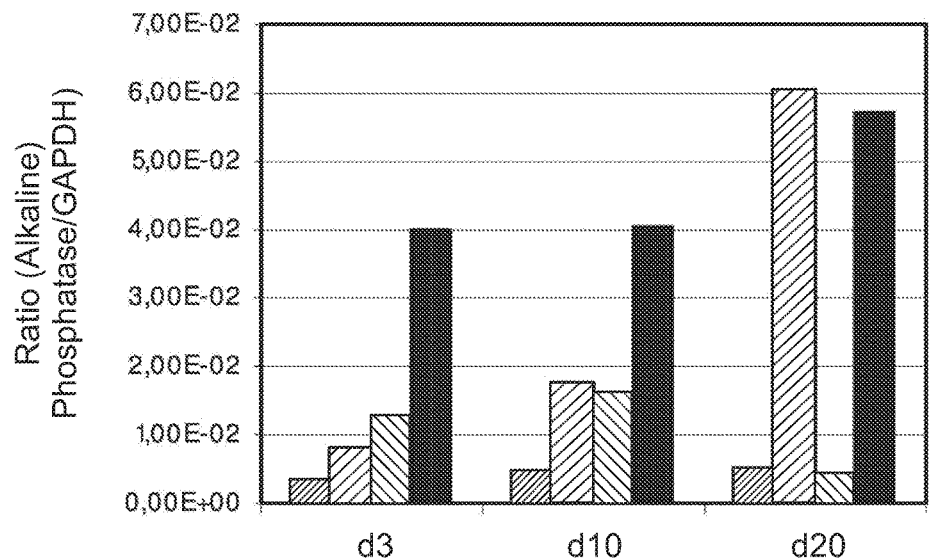
FIG. 3 shows the result of a quantitative PCR for the detection of the gene expression of osteogenesis-relevant markers. A: alkaline phosphatase; B: osterix; C: runx-2; D: osteocalcin. The ratio of expression level of the respective gene to that of the housekeeping gene GAPDH on day 3, 10 and 20 of the osteogenesis is shown.
Figure 3:
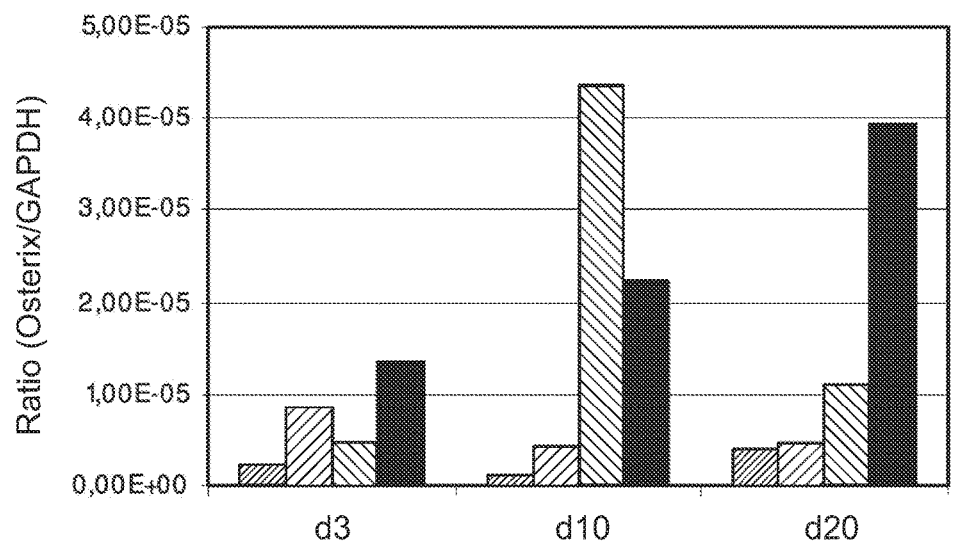
Figure 3:
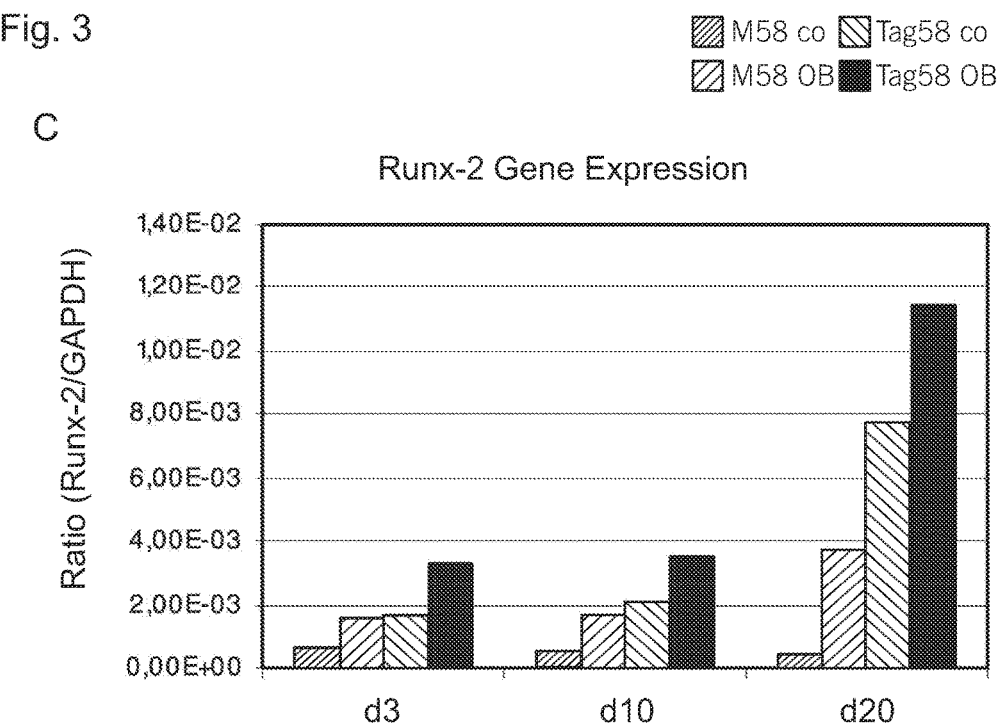
Figure 3:
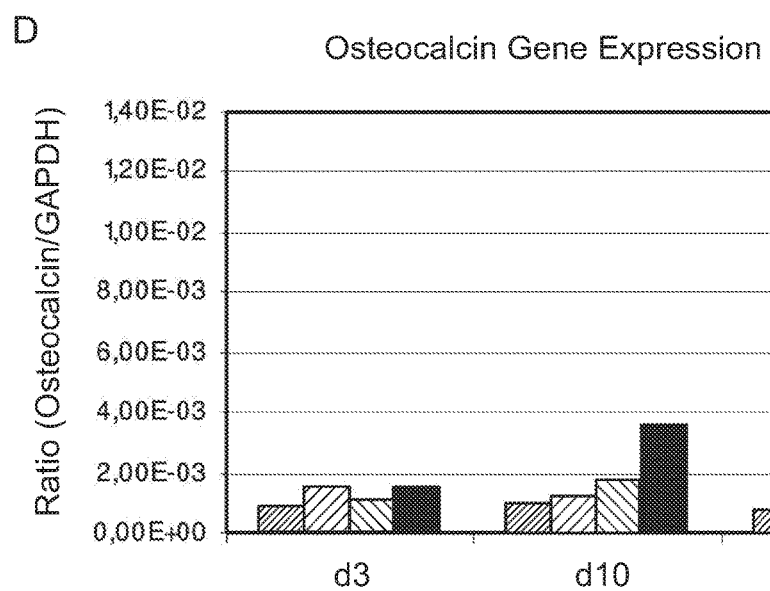

As shown in FIG. 3A, at the beginning and in the middle of osteogenesis (day 3 and 10) both higher basal level (Co) and higher inductions (OB) of alkaline phosphatase in the Tag58 cells were detectable by PCR. At the end of the differentiation (day 20) the mRNA levels become again more similar.

At all examined time points of osteogenesis higher basal level (Co) of the transcription factor osterix could be detected in the immortalized cells in comparison to the primary cells (FIG. 3B). With the exception of day 10 higher inductions (OB) were also detected in the Tag58 cells.

The quantitative examination of runx-2 gene expression showed at all three examined time points of osteogenesis higher levels in the Tag58 cells in comparison to the parental primary cells M58 (FIG. 3C).

The analysis of osteocalcin gene expression showed only on day 10 and 20 higher basal levels in the Tag58 cells, as can be seen in FIG. 3D.

Colorimetric Detection of Proliferation Activity

The detection of the proliferation activity was made by means of a semi-quantitative MTT-based colorimetric assay (EZ4U, Biozol). Through the conversion of tetrazolium salt to formazan derivatives in the mitochondria of the cell, conclusions about the cell vitality can be drawn. The results of the measured optic densities are summarized in the following table 1.

TABLE 1

Proliferation activities of primary (M58) versus Tag58 cells in an undifferentiated or differentiated state, determined by means of a colorimetric assay (EZ4U, Biozol). Listed are the optical densities ± standard deviation (n = 3).

|  | primary cells (M58) | | Tag58 cells (Tag58) | |
| --- | --- | --- | --- | --- |
|  | undifferentiated | osteogenically stimulated | undifferentiated | osteogenically stimulated |
| Day 3 | 0.419 ± 0.096 | 0.428 ± 0.051 | 0.569 ± 0.092 | 0.595 ± 0.232 |
| Day 10 | 1.527 ± 0.457 | 0.823 ± 0.100 | 2.222 ± 0.166 | 2.023 ± 0.185 |
| Day 20 | 2.390 ± 0.181 | 1.621 ± 0.247 | 2.090 ± 0.326 | 1.889 ± 0.145 |

The following findings were made: On day 3 of the osteogenic differentiation there were no significant differences between the parental primary cells (M58) and the Tag58 cells. The values of the optical density tend to be higher in the Tag58 cells, however, reached no significance niveau compared to the parental primary cells.

However, on day 10 of osteogenesis significant differences of the proliferation activity were shown. While osteogenic stimulated primary cells (M58) reduce their proliferation activity on medium-high OD values, the proliferation rates of undifferentiated and differentiated Tag58 cells are not significantly different, however, they are far above the OD values determined for primary cells.

On day 20 of osteogenesis no significant differences between the primary and the Tag58 cells could be detected.

Detection of the Mineralization Potential

Figure 4:
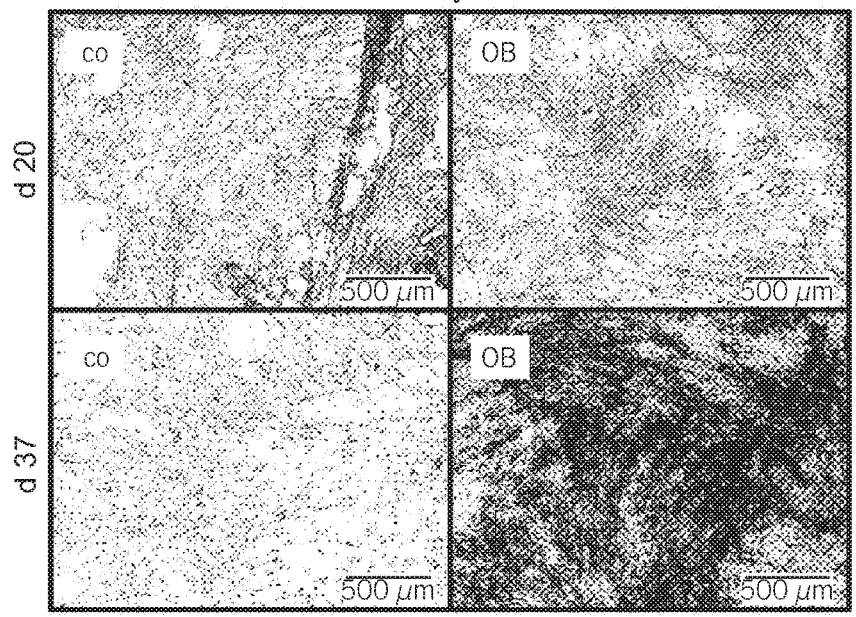
FIG. 4 shows the result of a microscopic examination for the detection of calcium phosphate precipitates with the aid of alizarin staining at different examination time points of the osteogenesis (day 16, d 16; day 20, d20; day 24, d 24; day 30, d 30; day 37, d 37), CO: undifferentiated cells; OB: osteogenically stimulated cells.
Figure 4:
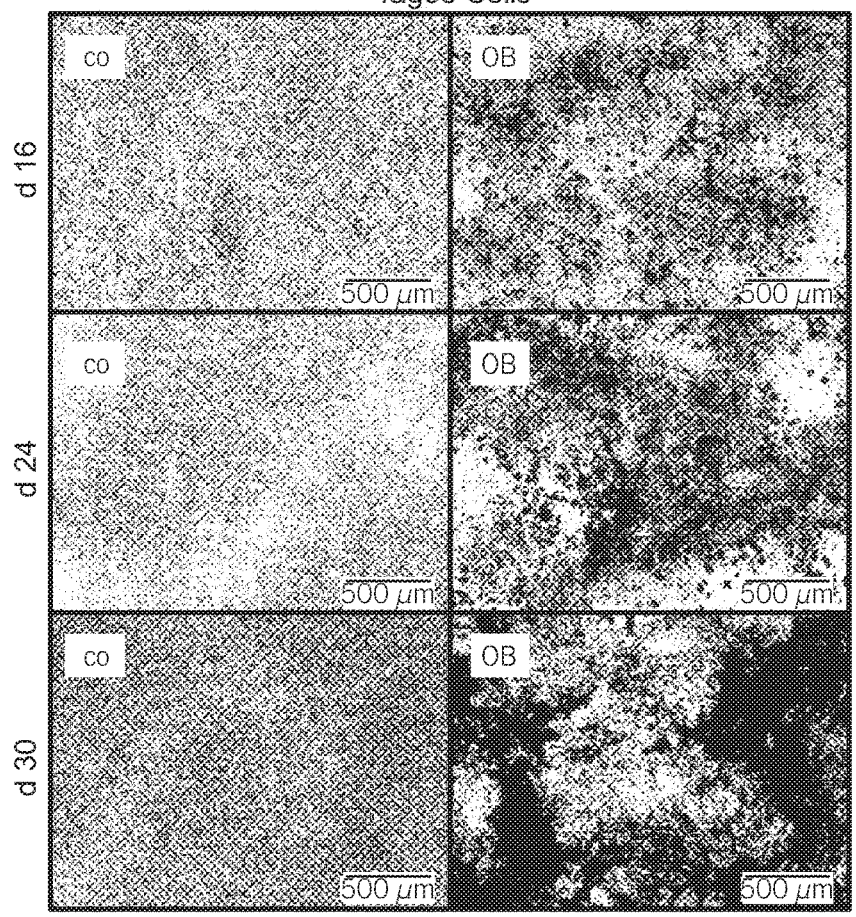

By means of the alizarin- or fluorescence-based Osteolmage staining calcium phosphate compositions can be detected (FIG. 3, FIG. 4), which are formed by mesenchymal precursor cells during the osteogenic differentiation process.

By means of the alizarin staining (FIG. 4) it could be detected that in the Tag58 cells the formation of the calcium phosphate precipitates occurs earlier than in the parental primary cells M58. This begins in the immortalized Tag58 cells already after 10 days of the osteogenic stimulation and is clearly detectable after 16 days (d 16) by means of alizarin staining (see FIG. 4). In contrast, a beginning of mineralization in the primary cells M58 was visible only after day 30 of the osteogenic stimulation and was detectable at day 37 (d 37) by means of alizarin staining.

Figure 5:
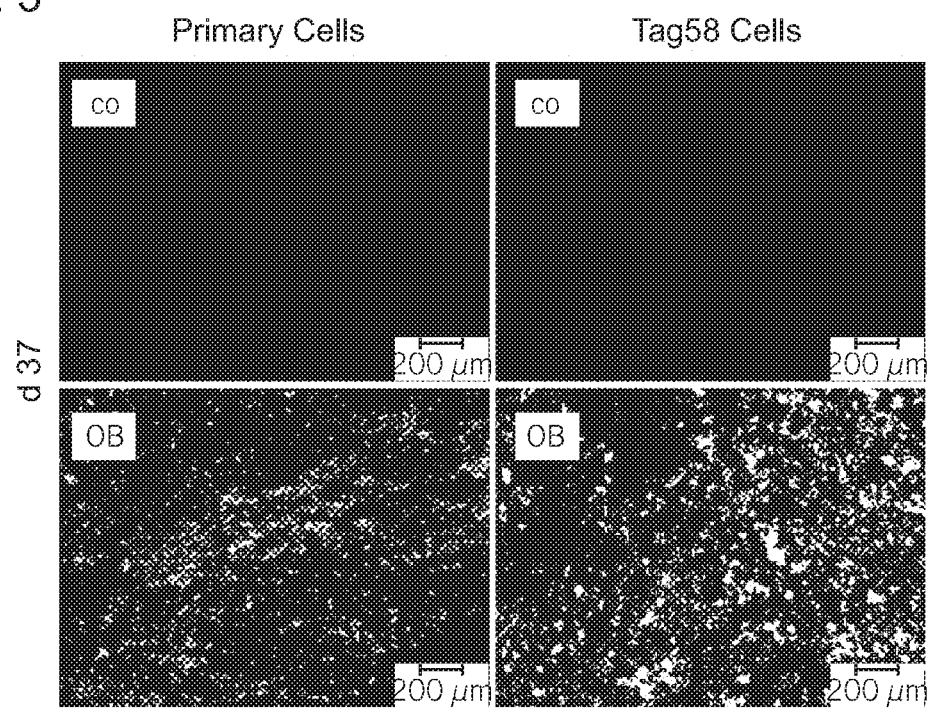
FIG. 5 shows the result of a microscopic examination with the aid of the osteoImage staining on day 37 (d 37) of the osteogenic stimulation for the detection of calcium phosphate precipitates. CO: undifferentiated cells; OB: osteogenetic stimulated cells.
Figure 6:
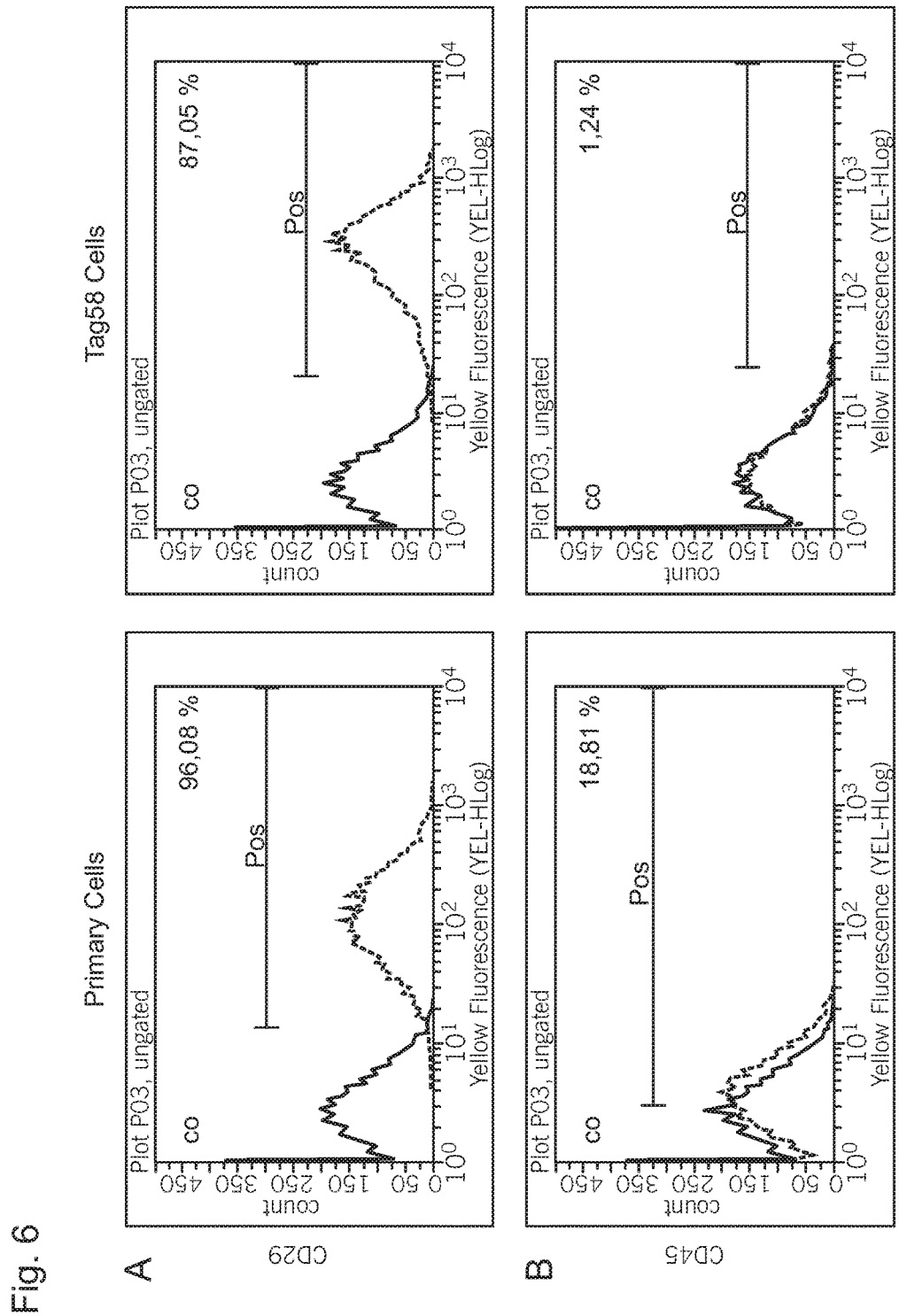
FIG. 6 shows the result of a flow cytometric examination for the detection of characteristic surface antigenes of the cell line in comparison to the parental cells.
Figure 6:
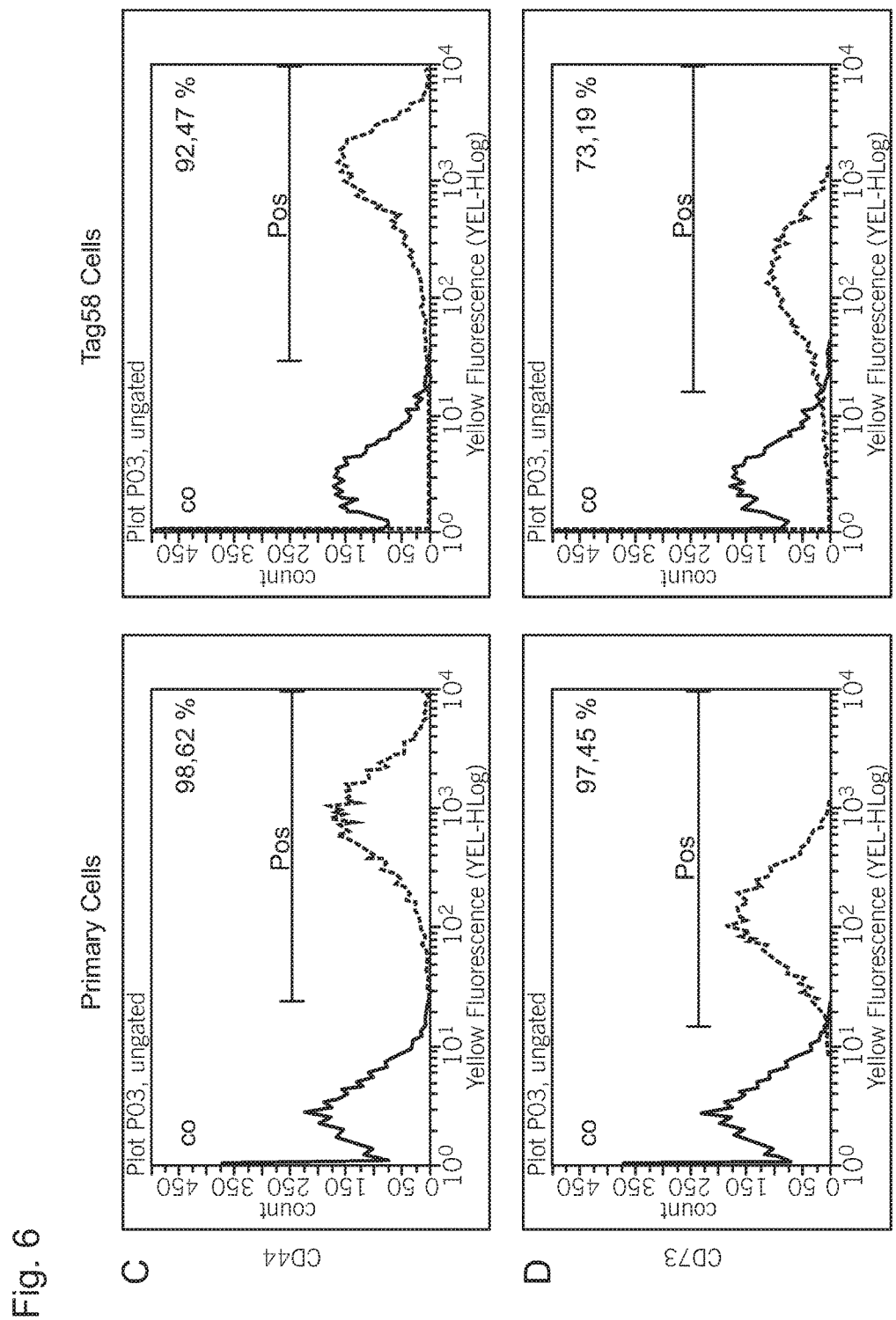
Figure 6:
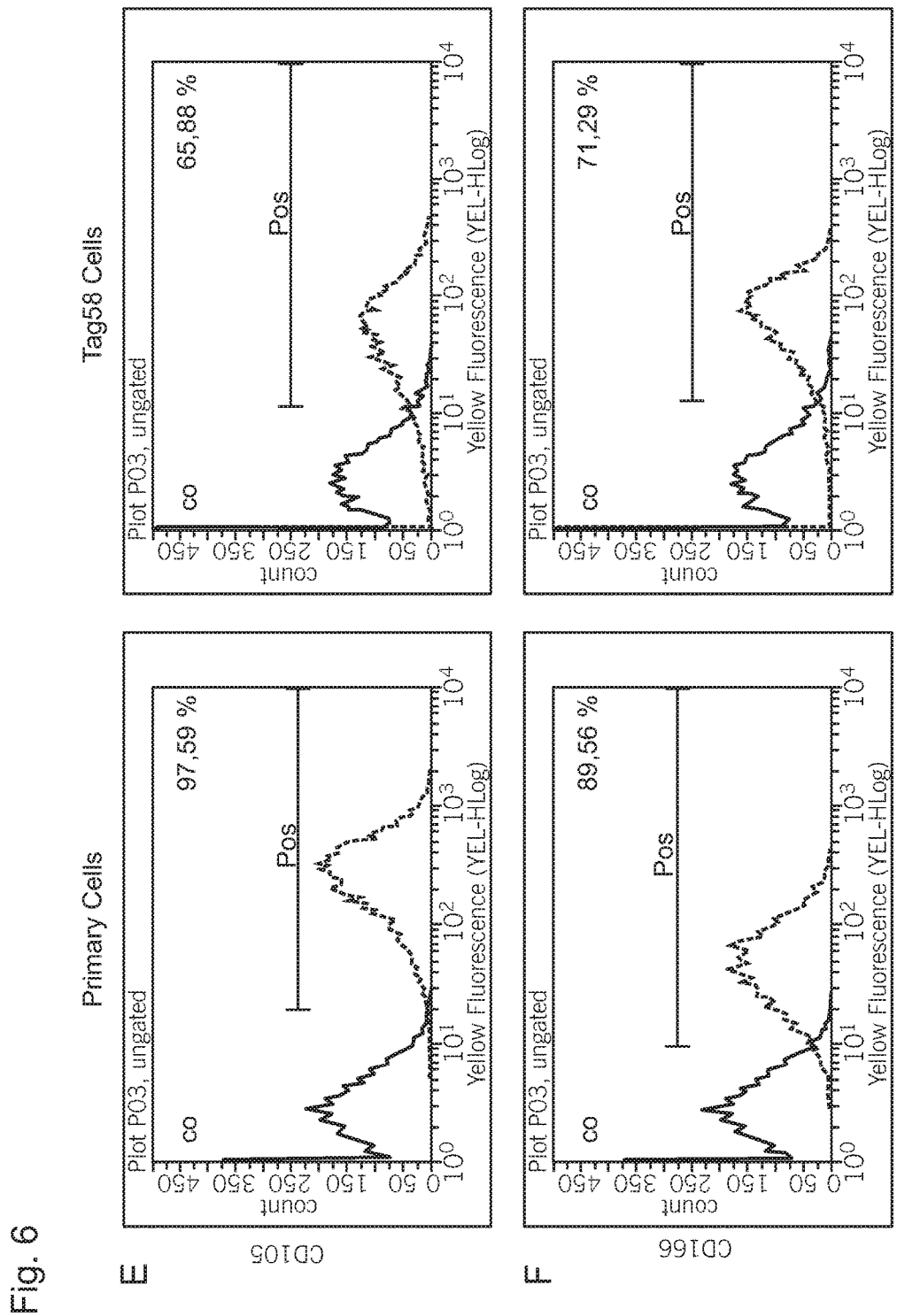
Figure 6:
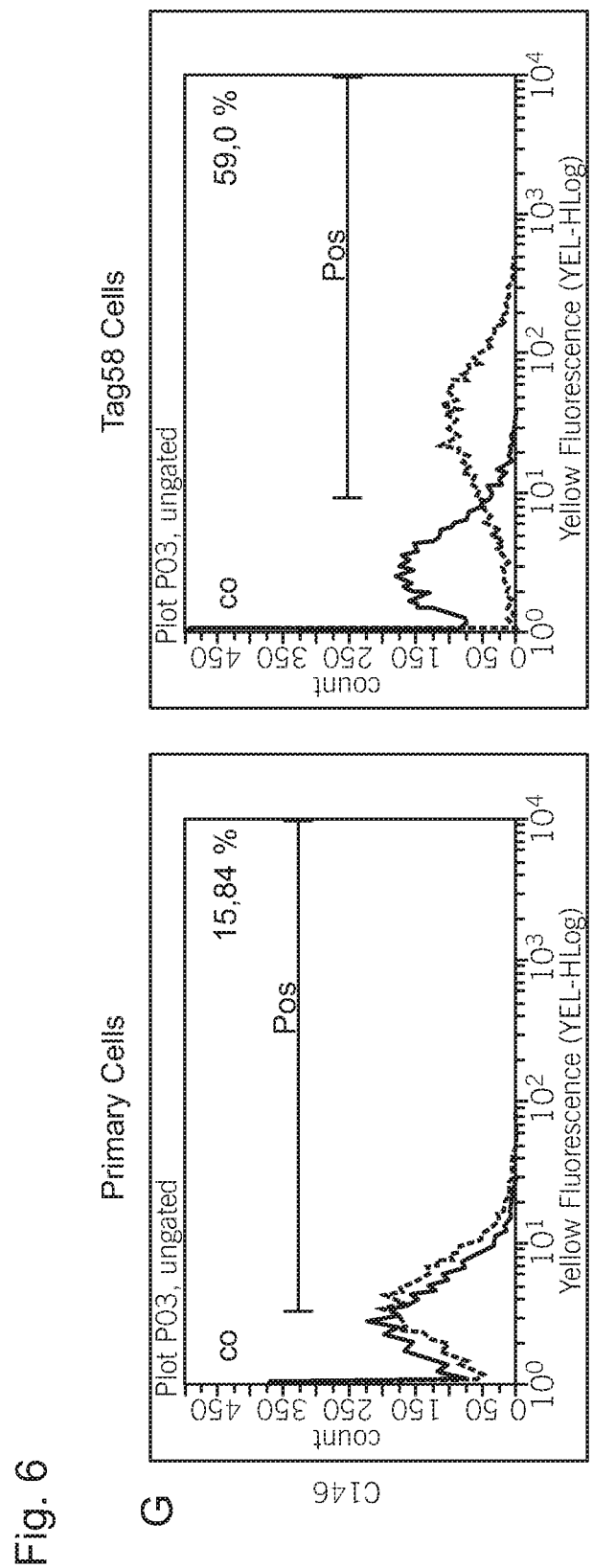

In a synchronized experiment at day 37 (d 37) an intensive Osteolmage staining of the calcium phosphate precipitate in the monolayer of the Tag58 cells could be detected, compared to the primary cells M58 (FIG. 5).

Flow Cytometric Investigations of the Surface Antigen Expression

Various surface antigens such as CD29, CD44, CD73, CD90, CD105 and CD166 have been defined as stem cell markers of mesenchymal stem cell lines. The surface marker expression was examined 10 days after seeding of the cells. CD45 is a leucocyte antigen that is mostly negative in cranium periosteum cells. The parental cells M58 from which the Tag58 cells according to the invention originated, however, show a weak CD45 expression (18.81%, see FIG. 5B). However, the Tag58 cells are almost negative with respect to the CD45 expression. The CD44, CD73, CD105, CD166 expressions showed in the primary as well as in the immortalized cells were relatively comparable (FIG. 5C-F) with the restriction that the percentage of the positive Tag58 for CD73, CD105 and CD166 was slightly lower. Surprisingly, a three-times higher CD146 expression in the Tag58 cells was detected in comparison to the primary cells (see FIG. 5G).

3 Conclusion

The inventor was able to confirm by means of a plurality of experimental evidences that starting from human primary cranium periosteum cells an immortalized periosteum cell line was generated.

Therefore, what is claimed is:

1. An isolated, in vitro immortalized cranium periosteum cell, wherein the cell was deposited on 29 Nov. 2013 under the designation "Tag58" at the Deutsche Sammlung von Mikroorganismen and Zellkulturen GmbH, Braunschweig, Germany (DSMZ) under the accession number DSM ACC3218.

2. A cell culture, which comprises a plurality of the isolated, in vitro immortalized cranium periosteum cells of claim 1.

3. A method for the production of an isolated, in vitro immortalized cranium periosteum cell deposited on 29 Nov. 2013 under the designation "Tag58" at the Deutsche Sammlunq von Mikroorganismen and Zellkulturen GmbH, Braunschweig, Germany (DSMZ) under the accession number DSM ACC3218, comprising the following steps:
   1) providing an isolated cranium periosteum primary cell, and
   2) immortalizing the cranium periosteum cell by transduction of the large T-antigen of the SV40 virus into the cranium periosteum primary cell.

* * * * *